United States Patent
Boroczky et al.

(10) Patent No.: US 10,943,697 B2
(45) Date of Patent: Mar. 9, 2021

(54) DETERMINING INFORMATION BASED ON AN ANALYSIS OF IMAGES AND VIDEO

(71) Applicant: International Business Machines Corporation, Armonk, NY (US)

(72) Inventors: Lilla Boroczky, Mount Kisco, NY (US); Francisco Phelan Curbera, Hastings on Hudson, NY (US); Maria Eleftheriou, Mount Kisco, NY (US); John R. Smith, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 348 days.

(21) Appl. No.: 15/828,806

(22) Filed: Dec. 1, 2017

(65) Prior Publication Data
US 2019/0172580 A1   Jun. 6, 2019

(51) Int. Cl.
*G16H 50/20*   (2018.01)
*G16H 10/60*   (2018.01)
*A01K 29/00*   (2006.01)
*A61B 5/16*   (2006.01)
*G06F 16/58*   (2019.01)
(Continued)

(52) U.S. Cl.
CPC ............. *G16H 50/20* (2018.01); *A01K 29/00* (2013.01); *A61B 5/0035* (2013.01); *A61B 5/0036* (2018.08); *A61B 5/0077* (2013.01); *A61B 5/165* (2013.01); *A61B 5/4848* (2013.01); *A61B 5/7267* (2013.01); *G06F 16/5866* (2019.01); *G06F 16/7867* (2019.01); *G16H 10/60* (2018.01); *A61B 2503/40* (2013.01)

(58) Field of Classification Search
CPC ............................... G16H 50/20; G16G 50/70
See application file for complete search history.

(56) References Cited

U.S. PATENT DOCUMENTS

| 2010/0131263 | A1* | 5/2010 | Angell | G10L 15/06 704/9 |
| 2017/0091403 | A1* | 3/2017 | Maher | G16H 10/40 |

FOREIGN PATENT DOCUMENTS

| CN | 204795385 U | 11/2015 |
| WO | WO-2012018218 A2 | 2/2012 |

(Continued)

OTHER PUBLICATIONS

"LifeLearn Sofie: Improving the health of patients and practices", LIfeLearn, Inc., © 2017, 5 pages, <http://www.lifelearn.com/lifelearn-sofie/>.

*Primary Examiner* — Sheetal R Paulson
(74) *Attorney, Agent, or Firm* — Daniel R. Simek (57) ABSTRACT

Aspects of the present invention disclose a method, computer program product, and system for identifying symptoms based on digital media. The method includes one or more processors receiving digital media and information associated with a first animal from a user. The method further includes one or more processors identifying data records, stored in a knowledge database, that are respectively associated with an animal that is similar to the first animal. The method further includes one or more processors determining symptom information corresponding to the first animal based on a comparison of the received digital media and information associated with the first animal and the identified data records. The method further includes presenting the determined symptom information to a user.

20 Claims, 3 Drawing Sheets

(51) Int. Cl.
*G06F 16/78* (2019.01)
*A61B 5/00* (2006.01)

(56) References Cited

FOREIGN PATENT DOCUMENTS

| WO | WO-2016059385 A1 | 4/2016 |
| WO | WO-2016060557 A1 | 4/2016 |

\* cited by examiner

DETERMINING INFORMATION BASED ON AN ANALYSIS OF IMAGES AND VIDEO

BACKGROUND

The present invention relates generally to the field of data analytics, and more particularly to machine learning.

In machine learning, a convolutional neural network (CNN, or ConvNet) is a class of deep, feed-forward artificial neural networks that has successfully been applied to analyzing visual imagery. CNNs use a variation of multilayer perceptrons, artificial neurons, designed to require minimal preprocessing. They are also known as shift invariant or space invariant artificial neural networks (SIANN), based on their shared-weights architecture and translation invariance characteristics.

Convolutional networks were inspired by biological processes in which the connectivity pattern between neurons is inspired by the organization of the animal visual cortex. Individual cortical neurons respond to stimuli only in a restricted region of the visual field known as the receptive field. The receptive fields of different neurons partially overlap such that they cover the entire visual field.

SUMMARY

According to one embodiment of the present invention, a method for identifying symptoms based on digital media is provided. The method for identifying symptoms based on digital media may include one or more processors receiving digital media and information associated with a first animal from a user. The method further includes one or more processors identifying data records, stored in a knowledge database, that are respectively associated with an animal that is similar to the first animal. The method further includes one or more processors determining symptom information corresponding to the first animal based on a comparison of the received digital media and information associated with the first animal and the identified data records. The method further includes presenting the determined symptom information to a user.

DETAILED DESCRIPTION

Embodiments of the present invention recognize that animal symptoms are observational by a pet owner or provided by a veterinarian assessment. Behavioral changes of the animals are often anecdotal by the pet owner and do not necessarily contain the most important information.

Embodiments of the present invention recognize that current approaches to clinical support to veterinarians is limited to question and answer approach based on natural language processing. Embodiments of the present invention recognize that current approaches do not provide decision support based on automatic symptom identification on video and images of an animal.

Embodiments of the present invention provide a method that automatically identifies symptoms based on video and image analysis. Embodiments of the present invention provide a method that detects abnormality in diagnostic images of a pet and a retrieval mechanism to consult similar animals of a database of animals with known diagnosis, treatment, and outcome.

Figure 1:
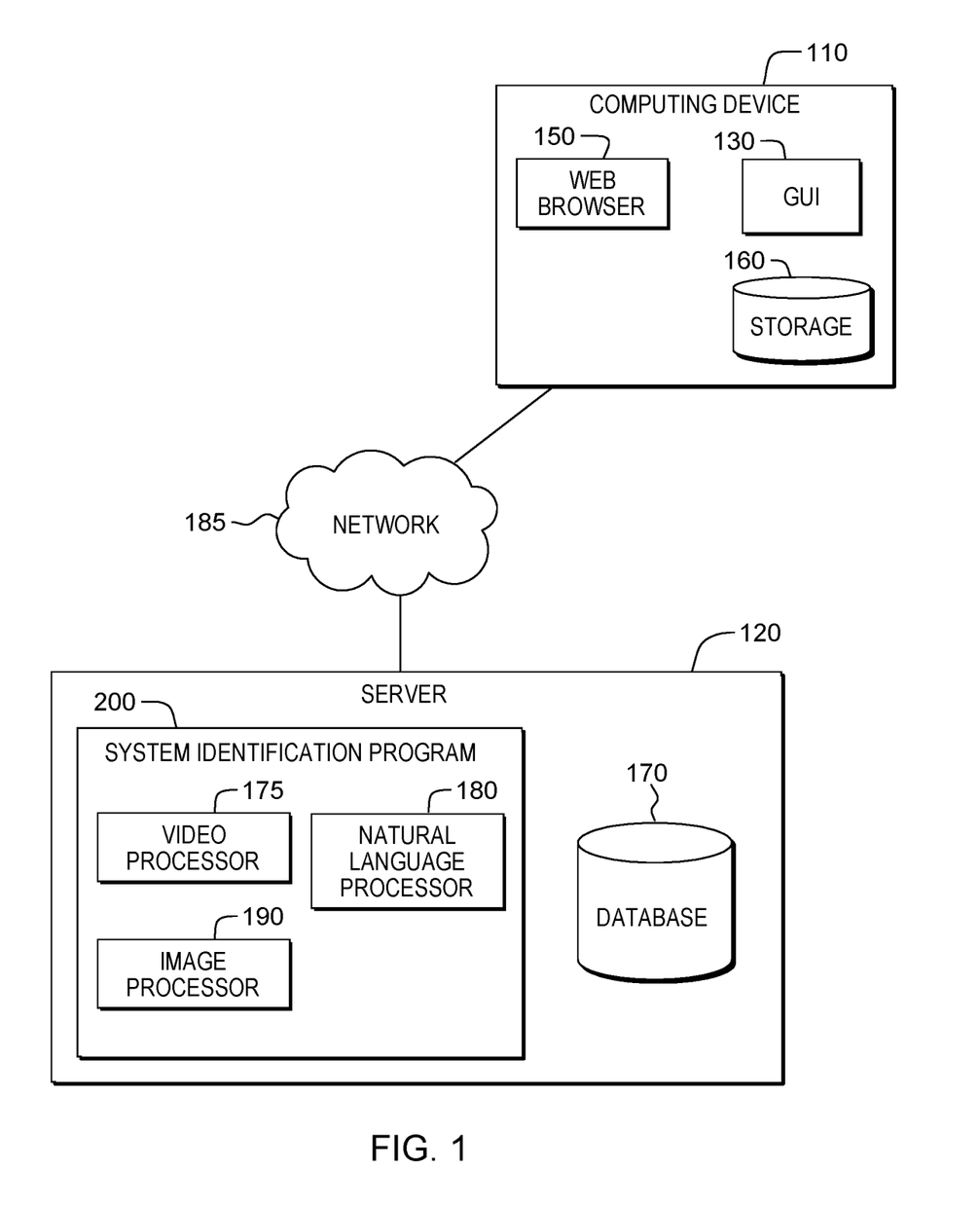
FIG. 1 is a functional block diagram illustrating a distributed data processing environment, in accordance with an embodiment of the present invention.

Example embodiments in accordance with the present invention will now be described in detail with reference to the Figures. FIG. 1 is a functional block diagram, illustrating distributed data processing environment 100. Distributed data processing environment 100 includes computing device 110, server 120, interconnected over network 185.

In one embodiment, computing device 110 includes graphical user interface (GUI) 130, web browser 150, and storage 160. The various programs on computing device 110 include a web browser, an electronic mail client, security software (e.g., a firewall program, a geo-locating program, an encryption program, etc.), an instant messaging (IM) application (app), and a communication (e.g., phone) application.

Computing device 110 may be a desktop computer, a laptop computer, a tablet computer, a specialized computer server, a smartphone, a wearable device (e.g., smart watch, personal fitness device, personal safety device), or any programmable computer system known in the art with an interactive display or any other computer system known in the art. In certain embodiments, computing device 110 represents a computer system utilizing clustered computers and components that act as a single pool of seamless resources when accessed through network 185, as is common in data centers and with cloud computing applications. In general, computing device 110 is representative of any programmable electronic device or combination of programmable electronic devices capable of executing machine-readable program instructions and communicating with other computer devices via a network.

In one embodiment, graphical user interface 130 operates on computing device 110. In another embodiment, graphical user interface 130 operates on another computer in a server based setting, for example on a server computer (e.g., server 120). In yet another embodiment, graphical user interface 130 operates on computing device 110 simultaneously with a server computer interconnected through network 185 (e.g., server 120). Graphical user interface 130 may be any user interface used to access information from computing device 110, such as information gathered or produced by program 200. Additionally, graphical user interface 130 may be any user interface used to supply information to computing device 110, such as information supplied by a user to be used by program 200. In some embodiments, graphical user interface 130 may present a generic web browser used to retrieve, present, and negotiate resources from the Internet. In other embodiments, graphical user interface 130 may be a software or application that enables a user at computing device 110 access to network 185.

In yet another embodiment, a user of computing device 110 can interact with graphical user interface 130 through a touch screen that performs as both an input device to a graphical user interface (GUI) and as an output device (i.e., an electronic display) presenting a plurality of icons associated with software applications or images depicting the executing software application. Optionally, a software application (e.g., a web browser) can generate graphical user interface 130 operating within the GUI of computing device 110. Graphical user interface 130 accepts input from a plurality of input/output (I/O) devices including, but not limited to, a tactile sensor interface (e.g., a touch screen or a touchpad) referred to as a multi-touch display. An I/O device interfacing with graphical user interface 130 may be connected to computing device 110, which may operate utilizing wired (e.g., USB port) or wireless network communications (e.g., infrared, NFC, etc.). Computing device 110 may include components, as depicted and described in further detail with respect to FIG. 3, in accordance with embodiments of the present invention.

Web browser 150 may be a generic web browser used to retrieve, present, and traverse information resources from the Internet. In some embodiments, web browser 150 may be a web browser designed for a mobile device. In other embodiments, web browser 150 may be a web browser designed for a traditional computing device, such as a desktop computer, PC, or laptop. In general, web browser 150 may be any application or software that enables a user of computing device 110 to access a webpage over network 185. In the depicted environment, web browser 150 resides on computing device 110. In other embodiments, web browser 150, or similar web browsers, may reside on other computing devices capable of accessing a webpage over network 185.

Storage 160 (e.g., a database) located on computing device 110, represents any type of storage device capable of storing data that is accessed and utilized by computing device 110. In other embodiments, storage 160 represents multiple storage devices within computing device 110. Storage 160 stores information such as, but not limited to, account information, credentials for authentication, user preferences, lists of preferred users, previously visited websites, history of visited Wi-Fi portals, observational videos of animals, and images of animals. For example, storage 160 stores images and videos of animals that can be retrieved and presented to a user in order to compare images of animals with a known diagnosis and treatment. In another example, storage 160 stores keywords retrieved from a knowledge database such as a scientific journal database, medication database, and symptom database.

In general, network 185 can be any combination of connections and protocols that will support communications among computing device 110. Network 185 can include, for example, a local area network (LAN), a wide area network (WAN), such as the Internet, a cellular network, or any combination of the preceding, and can further include wired, wireless, and/or fiber optic connections.

Server 120 may be a desktop computer, a laptop computer, a tablet computer, a specialized computer server, a smartphone, or any other computer system known in the art. In certain embodiments, server 120 represents a computer system utilizing clustered computers and components that act as a single pool of seamless resources when accessed through network 185, as is common in data centers and with cloud computing applications. In general, server 120 is representative of any programmable electronic device or combination of programmable electronic devices capable of executing machine-readable program instructions and communicating with other computer devices via a network. In one embodiment, server 120 includes database 170 and program 200.

In one embodiment, program 200 operates on server 120. In another embodiment, program 200 operates on another computer in a server based setting, for example on a server computer not shown. In yet another embodiment, program 200 operates on computing device 110 simultaneously with server 120 interconnected through network 185. Program 200 provides the capability automatically identify symptoms based on videos and image analytics. Program 200 is capable of utilizing Wi-Fi technology, Bluetooth, Near Field Communication tags (NFC), Global System for Mobile Communications (GSM), and Global Positioning System Technology (GPS) to communicate with computing device 110.

Database 170 may be a repository that may be read by program 200. In an example embodiment, database 170 can include information such as clinical databases, comprehensive animal databases and other information. In some embodiments, database 170 may access and retrieve information from other veterinary and clinical databases. In other embodiments, a program on server 120 (not shown) may prompt and update database 170 with information. The data stored to database 170 may be changed or updated by data input by a user, such as a user with access to server 120. In one embodiment, database 170 resides on server 120. In other embodiments, database 170 may reside on another server, another computing device, or mobile device, provided that database 170 is accessible to program 200.

Video processor 175 (a sub program of program 200) operates on server 120. Video processor 175 provides the capability to transform videos into analytically prepared data. In an embodiment, video processor 175 can receive user preferences for transforming videos or multimedia of interest to the user through segmenting videos and extracting low level and high-level features in the video. In an example embodiment, video processor 175 segments videos using algorithms and digital processing techniques known as video segmentation. The video segments transformed by video processor 175 are spatially relevant regions of image or video scenes that have a common set of features. The common features can be color distributions, intensity levels, texture, moving and stationary parts of a video.

In an example, video processor 175 segments a video into structured elements and prepares the video for feature extraction through identification of low-level features in the video. In this example, video processor 175 uses image segmentation algorithms that detect boundary, edges, and curves in a video, brightness gradients, texture gradients, color gradients, contour maps, multi-scale gradient magnitude, and video scene segments. Video processor 175 detects higher-level characteristics through storing the segmented low-level features in each instance. Video processor 175 extracts the higher-level characteristics of the video using algorithms that determine three-dimensional color histograms as "color fingerprints" of images, detect edges by analyzing intensity gradient around every pixel, detect corners using differential geometry operators, detect movement vectors and fields from video sequences associated with moving video segments, and combine sequences of common features across video sub-sequences. Video processor 175 detects the relationships between these features, variables and time and extracts the variables with time-stamped values.

Natural language processor 180 (a subprogram of program 200) is an advanced natural language processor drive sub program designed to retrieve syntactic information from knowledge resources. Natural language processor 180 is an information retrieval based knowledge resource feature extractor. In general, natural language processor 180 accesses a veterinary clinical database to identify and analyze text using the concept unique identifier. A concept unique identifier is a sub program of natural language processor 180 that selects and extracts the unique concept from the entirety of the text. The unique concept is the longest, complete phrase that has been identified through the knowledge resource. For example, natural language processor 180, utilizing the concept unique identifier in consultation with the knowledge resource and selects the unique concept, "obsessive compulsive disorder" (OCD) from the text and analyzes the text in conjunction with the entirety of the text to "obsessive" and "compulsive disorder." Natural language processor 180, utilizing concept unique identifier, is able to determine that "obsessive compulsive disorder" is a unique concept through sub dividing the word and cross referencing the entirety of the text and each individual component of the text, as described in the previous sentence, with a knowledge database.

In an embodiment, natural language processor 180 can utilize (not shown) a raw text reader and markable reader to detect sentences. A markable reader is a named entity recognizer that discovers groups of textual mentions that belong to a semantic class. Comprehensively, natural language processor 180 employs a tokenizer, tagger, word dependency parser, and constantly accesses the veterinary medical dictionary to determine and separate sentences and phrases of clinical relevance from sentences and phrases that do not have medical relevance. In the event that natural language processor 180 is unable to identify a concept unique identifier of medical relevance in a phrase, then a word parser analyzes the phrase.

In another embodiment, natural language processor 180 uses a mention recognizer to enable program 200 to analyze, recognize, and retrieve a set of key elements from large amounts of unstructured and structured clinical data. In an embodiment, mention recognizer analyzes a combination of unstructured and structured clinical notes.

Image processor 190 (a sub program of program 200) utilizes deep learning techniques, such as many layered convolutional neural networks to transform images into analytically prepared data. Image processor 190 utilizes a similar processor as video processor 175 to detect and classify visual images. Image processor 190 has the capability to be detect and classify millions of individual images and hundreds of object classes. In an embodiment, image processor 190 provides the capability to transform images into analytically prepared data. Image processor 190 can receive user preferences for transforming images of interest to the user through segmenting videos and extracting low level and high-level features in the video. In an example embodiment, image processor 190 segments images using algorithms and digital processing techniques known as image segmentation. The images transformed by image processor 190 are spatially relevant regions of images that have a common set of features. The common features can be color distributions, intensity levels, texture, moving and stationary parts of a video.

In an example, image processor 190 segments an image for breed identification of a cat. Image processor 190 segments the image into structured elements and prepares the image of the cat for feature extraction through identification of low-level features in the image of the cat. In this example, image processor 190 uses image segmentation algorithms that detect boundary, edges, curves in the image of the cat, brightness gradients, texture gradients, and color gradients of the image of the cat. Image processor 190 detects higher-level characteristics through storing the segmented low-level features of the image of the cat. Image processor 190 extracts the higher-level characteristics of the image using algorithms that determine three-dimensional color histograms as "color fingerprints" of the image of the cat associated with a particular species of the cat. Image processor 190, utilizing a similar animal retrieval unit, detects the relationships between these features and variables to automatically identify the breed of the cat.

In an embodiment, server 120 is capable of initiating a handshake process between server 120 and computing device 110. Handshaking is an automated process of negotiation that dynamically sets parameters of a communications channel established between two entities before normal communication over the channel begins. Handshaking follows the physical establishment of the channel and precedes normal information transfer. Handshaking facilitates connecting heterogeneous computing systems, or equipment, over a communication channel without the need for user intervention to set parameters. In an example, server 120 initiates the handshake process by sending a massage to computing device 110 indicating that server 120 wants to establish a communication channel in order to gain access to programs on computing device 110.

Figure 2:
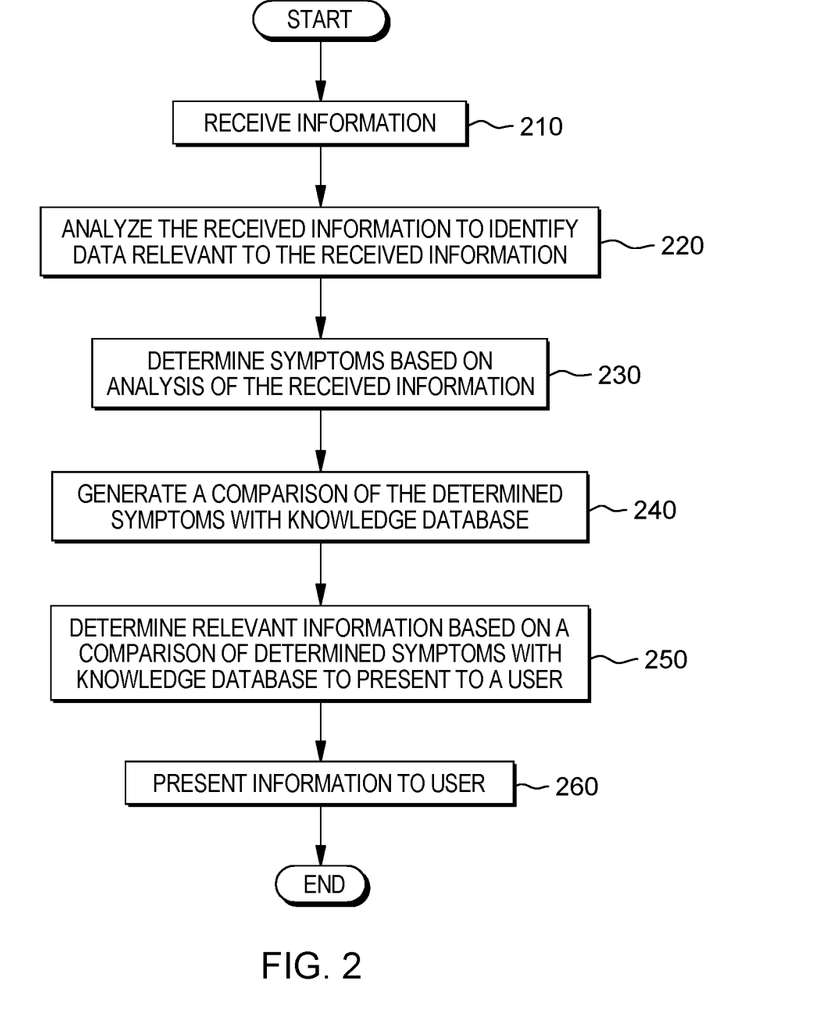
FIG. 2 is a flowchart depicting operational steps of program 200, a program for automatically identifying symptoms based on video and image media, in accordance with an embodiment of the present invention.

FIG. 2 is a flowchart depicting operational steps program 200, a program for automatically identifying symptoms based on video and image media, in accordance with an embodiment of the present invention.

In step 210, program 200 receives information. In an embodiment, program 200 receives information from a plurality of sources. In an example, program 200 identifies input from a health care provider using speech recognition utilizing natural language processor 180, In this example, program 200 receives animal type, demographics, medical history, symptoms, and vital signs of an animal. In this example, program 200 receives input, via natural language processor 180 that details the medical history of the animal as dictated by the owner of the animal.

In another embodiment program 200 receives an image of a pet through image processor 190. In an example, the dog is visiting a veterinarian practice for the first time. Program 200, through image processor 190, receives an image of the dog and identifies the species of the dog.

In step 220, program 200 analyzes the received information to identify data relevant to the received information. In an embodiment, program 200 analyzes the information received in step 210 to determine the relevant data. In an example, program 200 automatically searches one or more databases of scientific literature to determine the relevant data that program 200 can utilize to make a diagnosis of the animal based upon the received image.

In another embodiment, program 200 analyzes received observational videos, images, and input from a veterinarian. In an example, program 200 analyzes the x-rays and ultrasound images of an animal received in step 210. In this example, program 200 analyzes x-ray and the ultrasound images of the animal using deep learning techniques, for example convolutional neural networks. In an additional embodiment, program 200 can receive and analyze computed tomography (CT) scans and positron emission tomography (PET) scans associated with of an animal.

In step 230, program 200 determines symptoms based on analysis of the received information. In an embodiment, program 200 analyzes the information received in step 210 to determine the relevant data. Program 200 automatically searches one or more databases of scientific literature to determine the relevant data that program 200 utilizes to determine symptoms of the animal based upon the received image. In an example, program 200 utilizes the information, analyzed in step 220, to search scientific literature databases for animal breed, symptoms similar to the image of the animal, images of similar abnormalities, and past cases stored in a knowledge database. Program 200 utilizes the information received to determine symptoms of a disease in the animal.

In another embodiment, program 200 utilizes a search engine to identify the most relevant journal articles from one or more knowledge databases based upon analyzing the received information and identifying data that is relevant from the information received in step 220. In an example, program 200 receives images of an animal (in step 210). In this example, program 200 analyzes the images received in step 210 to identify the animal type, the animal breed, the symptoms of the animal, and to identify symptoms of disease in the animal. In this example, program 200 identifies the journal articles most relevant to canine species of a German Shepard dog. Program 200 utilizes the information from the image of the German Shepard to determine symptoms of the animal's illness.

In another embodiment, program 200 analyzes a series of videos received over a defined time period to observe a progression of the animal's behavior. In this example, program 200, receives information in step 210, in the form of a series of video clips that display the animal's response to multiple stimuli. In this example, program 200 analyzes twelve distinct video clips of an animal, with different stimuli such as playing with a pet toy, presenting food to the animal, over the course of twelve months to identify relevant data. Program 200, through video processor 175, combines the clips into one complete video stream showing the progression of the symptoms revealed through receipt of animal health record information, and x-ray information in step 210. The video clips reveal degenerative symptoms that cause a change in the gait of the animal over a defined time period. Program 200 analyzes information from scientific knowledge databases using a search engine to determine the symptoms of the animal as consistent with the symptoms of the disease in a knowledge database.

In another example, program 200, through GUI 130, receives a dictation of symptoms from a user. In this example, program 200 utilizes natural language processor 180 to identify words, from the dictation received from the user, that are associated with diseases in one or more knowledge databases to determine one or more symptoms of the animal from the received dictation.

In step 240, program 200 generates a comparison of the determined symptoms with knowledge database. In an embodiment, program 200 utilizes the symptoms, determined in step 230, to retrieve similar animal breeds with similar symptoms with a known diagnosis to compare to the determined symptom information. In an example, program 200 utilizes the video that a pet owner recorded on unwanted repetitive behavior in their pet (received in step 210). Program 200 identifies a snapshot from the video clip and analyzes the pet's behavior by comparing the pet's behavior to similarities and patterns in videos and images from a veterinary knowledge resource that contains information of a similar animal with a known diagnosis and treatment plan.

In another example, program 200 utilizes a similar animal retrieval unit, a sub program of program 200, to compare the images of the x-rays of the German Shepard skeleton with images of healthy German Shepard skeletons and images of abnormal German Shepard skeletons that have a similar injury as revealed through images of similarly abnormal German Shepard skeletons in one or more knowledge databases. Program 200 compares the animal demographic, medical history and vital sign information with identified abnormalities in one or more scientific literature databases that are associated with a similar medical history.

In another embodiment, program 200 combines the determined symptoms from step 230 with abnormalities detected by diagnostic veterinarian images of the animal, and pet owner descriptions of the symptoms and veterinarian assessment. In an example, program 200 uses the aggregated symptoms to identify similar animals from a database of animals with known diagnosis, treatment plan, and outcome. In this example, program 200 utilizes a search engine to identify the most relevant academic papers to the particular breed of animal and the symptoms that the animal is experiencing.

In step 250, program 200 determines relevant information based on a comparison of the determined symptoms with knowledge database to present to a user. In an embodiment, program 200 presents relevant information, based on breed, the disease abnormality, and the diagnosis, for a particular animal based on the symptoms determined from step 230 and a comparison of the symptoms from step 240. In an example, program 200 determines that the calculated drug and drug dosage for a cat in a knowledge database are correlated with symptoms identified from a comparison of a cat patient with one or more similar cats with a known diagnosis in a knowledge database. In another example, program 200 determines that symptoms from the collected observational videos, images, and input from the veterinarian are relevant because the symptoms correlate strongly, through comparison, with symptoms indicated in one or more academic journals as being a conclusory indication of a particular disease.

In another example, program 200 utilizes the information determined in step 230 to direct a search engine to locate information, from one or more knowledge resources, of the same breed, demographic, with similar symptoms, a known diagnosis, and a similar treatment plan and outcome for the animal. In this example, program 200 aggregates the treatment plan information with the symptoms determined for an animal in step 230 to determine that the information is relevant to diagnosing the symptoms of the animal.

In step 260, program 200 presents the determined information to the user. In an embodiment, program 200 presents symptom information to the user through GUI 130. In an example, program 200 analyzes a diagnostic image of a dog's liver. Program 200 utilizes the similarity retrieval sub program to retrieve similar images, from a knowledge database, of other dogs with a known diagnosis, treatment plan, and outcome. Program 200 presents the similar images from the knowledge database to the user.

In another embodiment, program 200 can serve as a triage tool for the pet owner based on the symptoms entered by a pet owner and identified from the pet images and video. In an example, program 200 can present advice to an owner whether to make a veterinarian appointment or to take the animal to an emergency room. In this example, program 200 augments a global online system of pet health information. In another example, program 200 present a drug list with recommended dosages and drug interactions are displayed on GUI 130 on computing device 110.

Figure 3:
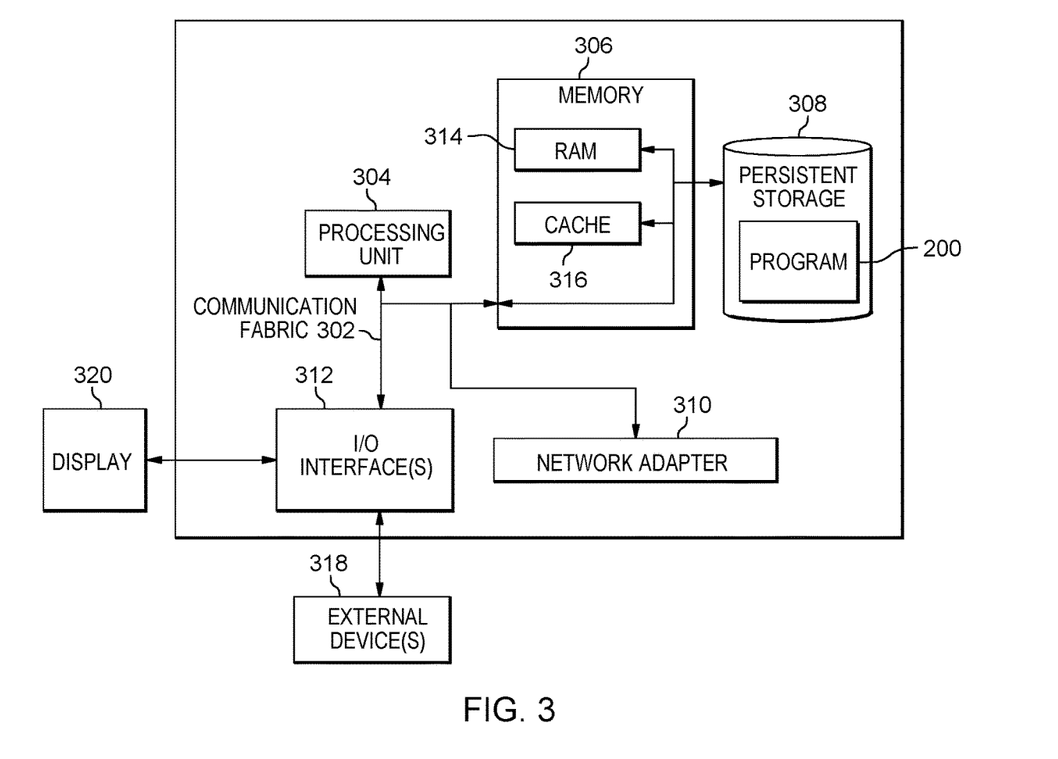
FIG. 3 is a block diagram of components of a computer system, such as the server computer of FIG. 1, in an embodiment in accordance with the present invention.

FIG. 3 depicts a block diagram of components of server 120 in accordance with an illustrative embodiment of the present invention. It should be appreciated that FIG. 3 provides only an illustration of one implementation and does not imply any limitations with regard to the environments in which different embodiments may be implemented. Many modifications to the depicted environment may be made.

Server 120 includes communications fabric 302, which provides communications between cache 316, memory 306, persistent storage 308, communications unit 310, and input/output (I/O) interface(s) 312. Communications fabric 302 can be implemented with any architecture designed for passing data and/or control information between processors (such as microprocessors, communications and network processors, etc.), system memory, peripheral devices, and any other hardware components within a system. For example, communications fabric 302 can be implemented with one or more buses or a crossbar switch.

Memory 306 and persistent storage 308 are computer readable storage media. In this embodiment, memory 306 includes random access memory (RAM). In general, memory 306 can include any suitable volatile or non-volatile computer readable storage media. Cache 316 is a fast memory that enhances the performance of computer processor(s) 304 by holding recently accessed data, and data near accessed data, from memory 306.

Program 200 may be stored in persistent storage 308 and in memory 306 for execution by one or more of the respective computer processors 304 via cache 306. In an embodiment, persistent storage 308 includes a magnetic hard disk drive. Alternatively, or in addition to a magnetic hard disk drive, persistent storage 308 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 308 may also be removable. For example, a removable hard drive may be used for persistent storage 308. Other examples include optical and magnetic disks, thumb drives, and smart cards that are inserted into a drive for transfer onto another computer readable storage medium that is also part of persistent storage 308.

Communications unit 310, in these examples, provides for communications with other data processing systems or devices. In these examples, communications unit 310 includes one or more network interface cards. Communications unit 310 may provide communications through the use of either or both physical and wireless communications links. Program 200 may be downloaded to persistent storage 308 through communications unit 310.

I/O interface(s) 312 allows for input and output of data with other devices that may be connected to server 120. For example, I/O interface 312 may provide a connection to external devices 318 such as a keyboard, keypad, a touch screen, and/or some other suitable input device. External devices 318 can also include portable computer readable storage media such as, for example, thumb drives, portable optical or magnetic disks, and memory cards. Software and data used to practice embodiments of the present invention, e.g., program 200, can be stored on such portable computer readable storage media and can be loaded onto persistent storage 308 via I/O interface(s) 312. I/O interface(s) 312 also connect to a display 320. Display 320 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method for identifying symptoms based on digital media, the method comprising:
   receiving, by one or more processors, digitized image media and information associated with a first animal;
   extracting, by the one or more processors, low-level and high-level features of spatially relevant regions of the digitized image media by image segmenting the digital image media and information by a digital processing technique of image segmenting;
   generating, by the one or more processors, analytical data including symptom information from the digital image media that is received, based on applying the extracted low-level and hi-level features of the spatially relevant regions of the digitized image media as input to a multi-layer convolutional neural network;
   determining, by the one or more processors, an animal type, a breed type, and features associated with the first animal, based on the analytical data from the digitized image media that is received;
   identifying, by one or more processors, medical history data records, stored in a knowledge database, that are respectively associated with an animal that is similar to the first animal, based on applying natural language processing to unstructured data accessed in the knowledge database;
   generating, by one or more processors, a diagnosis based on the symptom information corresponding to the first animal by a comparison of the generated output of the analytical data from the multi-layer convolutional neural network to the identified medical history data records of the animal that is similar to the first animal; and
   presenting, by one or more processors, the diagnosis corresponding to the symptom information.

2. The method of claim 1, wherein the received digital image media and information is selected from the group consisting of:
   animal demographics, medical history, animal symptoms, animal vital signs, scanned images, x-rays, ultrasounds, computed tomography (CT) scans, and positron emission tomography (PET) scans.

3. The method of claim 1, wherein the symptom information corresponding to the first animal further comprises:
   retrieving, by one or more processors, information from a plurality of knowledge databases associated with an animal species that corresponds to the first animal based on the symptom information;
   determining, by one or more processors, a comparison of the retrieved information to the received digital image media and information associated with the first animal; and
   generating, by one or more processors, a treatment plan corresponding to the diagnosis for the first animal based on the comparison of the retrieved information to the received digital image media and information associated with the first animal.

4. The method of claim 1, wherein determining symptom information corresponding to the first animal further comprises:

identifying, by one or more processors, symptom information from audio media included in the received digital image media and information associated with the first animal; and aggregating, by one or more processors, the identified symptom information from the audio media with an assessment from a medical professional.

5. The method of claim 1, wherein identifying medical history data records, stored in a knowledge database further comprises:

retrieving, by one or more processors, data from a veterinary electronic medical record; and determining, by one or more processors, information related to a diagnosis and corresponding treatment plans of animals of a species that corresponds to the first animal from the veterinary electronic medical record.

6. The method of claim 1, wherein generating analytical data including symptom information corresponding to the first animal further comprises:

identifying, by one or more processors, a second animal that is associated with symptom information that corresponds to the symptom information of the first animal;

determining, by one or more processors, a treatment plan and corresponding outcome for the second animal; and generating, by one or more processors, a treatment plan for the first animal utilizing the determined treatment plan and corresponding outcome for the second animal.

7. The method of claim 1, wherein the digital image media includes consolidated segments of video images of the first animal taken over a designated period of time.

8. The method of claim 1, wherein generating analytical data including symptom information from the digital image media that is received, based on applying neural network deep learning techniques, further comprises:

program instructions to perform image segmentation techniques on the digital image media that is received; and program instructions to detect common features, boundaries, edges, and gradients within the digital image media.

9. The method of claim 1, wherein the low-level features include boundaries, curves, brightness gradients, texture gradients, and color gradients, and wherein the high-level features include intensity gradient of respective pixels, movement vectors, and combination of common feature.

10. A computer program product for identifying symptoms based on digital media, the computer program product comprising:

one or more computer readable tangible storage media and program instructions stored on at least one of the one or more computer readable storage media, the program instructions readable/executable by one or more computer processors and further comprising:

program instructions to receive digitized image media and information associated with a first animal;

programming instructions to extract low-level and high-level features of spatially relevant regions of the digitized image media by image segmenting by image segmenting;

program instructions to generate analytical data including symptom information from the digital image media that is received, based on applying the extracted low-level and high-level features of the spatially relevant regions of the digitized image media as input to a multi-layer convolutional neural network;

program instructions to determine an animal type, a breed type, and features associated with the first animal, based on the analytical data from the digitized image media that is received;

program instructions to identify medical history data records, stored in a knowledge database, that are respectively associated with an animal that is similar to the first animal, based on applying natural language processing to unstructured data accessed in the knowledge database;

program instructions to generate a diagnosis based on the symptom information corresponding to the first animal by a comparison of the generated output of the analytical data from the multi-layer convolutional neural network to the identified medical history data records of the animal that is similar to the first animal; and presenting, by one or more processors, the diagnosis corresponding to the symptom information.

11. The computer program of claim 10, wherein program instructions to generate analytical data including the symptom information corresponding to the first animal further comprises program instructions, stored on the one or more computer readable storage media, which when executed by a processor, cause the processor to:

retrieve information from a plurality of knowledge databases associated with an animal species that corresponds to the first animal based on the symptom information;

determine a comparison of the retrieved information to the received digital image media and information associated with the first animal; and generate a treatment plan corresponding to the diagnosis for the first animal based on the comparison of the retrieved information to the received digital image media and information associated with the first animal.

12. The computer program of claim 10, wherein program instructions to determine symptom information corresponding to the first animal further comprises program instructions, stored on the one or more computer readable storage media, which when executed by a processor, cause the processor to:

identify symptom information from audio media included in the received digital image media and information associated with the first animal; and aggregate the identified symptom information from the audio media with an assessment from a medical professional.

13. The computer program of claim 10, wherein program instructions to identify medical history data records, stored in a knowledge database further comprises program instructions, stored on the one or more computer readable storage media, which when executed by a processor, cause the processor to:

retrieve data from a veterinary electronic medical record; and determine information related to a diagnosis and corresponding treatment plans of animals of a species that corresponds to the first animal from the veterinary electronic medical record.

14. The computer program of claim 10, wherein program instructions to generate analytical data including symptom information corresponding to the first animal further comprises program instructions, stored on the one or more computer readable storage media, which when executed by a processor, cause the processor to:

identify a second animal that is associated with the symptom information that corresponds to the symptom information of the first animal;

determine a treatment plan and corresponding outcome for the second animal; and generate a treatment plan for the first animal utilizing the determined treatment plan and corresponding outcome for the second animal.

15. The Computer Program Product of claim 10, wherein program instructions to generate analytical data including symptom information from the digital image media that is received, based on applying neural network deep learning techniques, further comprises:

program instructions to perform image segmentation techniques on the digital image media that is received; and program instructions to detect common features, boundaries, edges, and gradients within the digital image media.

16. A computer system for product for identifying symptoms based on digital media, the computer system comprising:

one or more computer processors;

one or more computer readable storage media; and program instructions stored on the one or more computer readable storage media for execution by at least one of the one or more computer processors, the program instructions comprising:

program instructions to receive digitized image media and information associated with a first animal;

program instructions to extract low-level and high-level features of spatially relevant regions of the digitized image media by image segmenting;

program instructions to generate analytical data including symptom information from the digital image media that is received, based on applying the extracted low-level and hi-level features of the spatially relevant regions of the digitized image media as input to a multi-layer convolutional neural network;

program instructions to determine an animal type, a breed type, and features associated with the first animal, based on the analytical data from the digital image media that is received;

program instructions to identify medical history data records, stored in a knowledge database, that are respectively associated with an animal that is similar to the first animal, based on applying natural language processing to unstructured data accessed in the knowledge database;

program instructions to generate a diagnosis base on the symptom information corresponding to the first animal by a comparison of the generated output of the analytical data from the multi-layer convolutional neural network to the identified medical history data records of the animal that is similar to the first animal; and program instructions to present the diagnosis corresponding to the symptom information.

17. The computer system of claim 16, wherein the received digital image media and information are selected from the group consisting of:

animal demographics, medical history, animal symptoms, animal vital signs, scanned images, x-rays, ultrasounds, computed tomography (CT) scans, and positron emission tomography (PET) scans.

18. The computer system of claim 16, wherein program instructions to present the symptom information further comprises program instructions, stored on the one or more computer readable storage media, which when executed by a processor, cause the processor to:

determine appropriate information to present to a user, wherein appropriate information is a treatment plan for the first animal.

19. The computer system of claim 16, wherein program instructions to generate analytical data including the symptom information corresponding to the first animal further comprises program instructions, stored on the one or more computer readable storage media, which when executed by a processor, cause the processor to:

retrieve information from a plurality of knowledge databases associated with an animal species that corresponds to the first animal based on the symptom information;

determine a comparison of the retrieved information to the received digital image media and information associated with the first animal; and generate a treatment plan and a corresponding diagnosis for the first animal based on the comparison of the retrieved information to the received digital image media and information associated with the first animal.

20. The computer system of claim 16, wherein program instructions to identify medical history data records, stored in a knowledge database further comprises program instructions, stored on the one or more computer readable storage media, which when executed by a processor, cause the processor to:

retrieve data from a veterinary electronic medical record; and determine information related to a diagnosis and corresponding treatment plans of animals of a species that corresponds to the first animal from the veterinary electronic medical record.

* * * * *